(12) United States Patent
Little, III et al.

(10) Patent No.: US 10,670,519 B2
(45) Date of Patent: Jun. 2, 2020

(54) REAL TIME CRUDE OIL VALIDATION SWEPT SOURCE SPECTROSCOPY

(71) Applicant: JP3 Measurement, LLC, Austin, TX (US)

(72) Inventors: Joseph Paul Little, III, Austin, TX (US); Matthew R. Thomas, Austin, TX (US)

(73) Assignee: JP3 Measurement, LLC, Austin, TX (US)

( * ) Notice: Subject to any disclaimer, the term of this patent is extended or adjusted under 35 U.S.C. 154(b) by 52 days.

(21) Appl. No.: 16/141,350

(22) Filed: Sep. 25, 2018

(65) Prior Publication Data
US 2019/0094137 A1      Mar. 28, 2019

Related U.S. Application Data

(60) Provisional application No. 62/562,690, filed on Sep. 25, 2017.

(51) Int. Cl.
| | | |
|---|---|---|
| *G01N 21/3577* | (2014.01) | |
| *G01N 21/39* | (2006.01) | |
| *G01N 33/28* | (2006.01) | |
| *G01N 21/85* | (2006.01) | |
| *G01N 21/359* | (2014.01) | |
| *G01N 21/84* | (2006.01) | |

(52) U.S. Cl.
CPC ......... *G01N 21/3577* (2013.01); *G01N 21/39* (2013.01); *G01N 21/85* (2013.01); *G01N 33/2823* (2013.01); *G01N 33/2841* (2013.01); *G01N 21/359* (2013.01); *G01N 2021/8416* (2013.01)

(58) Field of Classification Search
CPC ....... G01N 2021/8416; G01N 21/3577; G01N 21/359; G01N 21/39; G01N 21/85; G01N 33/2823; G01N 33/2841
See application file for complete search history.

(56) References Cited

U.S. PATENT DOCUMENTS

| 9,464,242 B2 * | 10/2016 | Kusinski ................ C10G 75/00 |
|---|---|---|
| 2005/0050009 A1 | 3/2005 | Gardner et al. |
| 2014/0278141 A1 | 9/2014 | Mertens |

(Continued)

OTHER PUBLICATIONS

International Search Report and Written Opinion dated Feb. 22, 2019, in corresponding International Patent Application No. PCT/US2018/052658.

*Primary Examiner* — Hina F Ayub
(74) *Attorney, Agent, or Firm* — DeBois, Bryant & Campbell, LLP; William D. Wiese

(57) ABSTRACT

A system of spectroscopic devices deployed amongst the fluid infrastructure of hydrocarbon fluids are described herein. The devices provide early visibility into the characteristics of those fluids which inform and educate downstream parties of the potential value of the fluid, or the opportunity to reblend or redirect the fluid to optimize the formulization. By allowing downstream parties to determine the quality and quantity of refined products at an early stage, they are better able to determine the true value of the fluid. The data from the distributed network of spectroscopic analyzers provides valuation information that can be used to make more informed purchasing decisions or allow processors to create blends that optimize the efficiency of refining operations.

15 Claims, 4 Drawing Sheets

(56) References Cited

U.S. PATENT DOCUMENTS

| | | |
|---|---|---|
| 2015/0047712 A1 | 2/2015 | Little, III et al. |
| 2016/0122658 A1* | 5/2016 | O'Rear .................... C10G 7/00 208/251 R |
| 2017/0007974 A1 | 1/2017 | Wright et al. |
| 2017/0023485 A1 | 1/2017 | Stubbins et al. |

* cited by examiner

REAL TIME CRUDE OIL VALIDATION SWEPT SOURCE SPECTROSCOPY

PRIORITY STATEMENT

Under 35 U.S.C. § 119 & 37 C.F.R. § 1.78

This non-provisional application claims priority based upon prior U.S. Provisional Patent Application Ser. No. 62/562,690 filed Sep. 25, 2017, in the names of Joseph Paul Little, III, and Matthew R. Thomas entitled "REAL TIME CRUDE OIL VALUATION VIA SWEPT SOURCE SPECTROSCOPY," the disclosures of which are incorporated herein in their entirety by reference as if fully set forth herein.

BACKGROUND OF THE INVENTION

The overall economics or viability of a refinery depends on the interaction of three key elements: the choice of crude oil used, called the crude slate, the refinery configuration, and the desired type and quality of products produced, called the product slate. In current practice, assumptions are made regarding the crude oil slates, and the value of that slate is determined based on the desired product slate.

Assumptions regarding the crude oil slate are based on many factors. Predominantly, the perceived value is based on historical knowledge of a slate. Lab tests are run and data is collected when a slate is run through a refinery distillation tower. These data points are correlated to relative density, also expressed as API Gravity (in degrees), which are the only metrics that can currently be accurately measured in the field.

The new diversity in the domestic supply of hydrocarbon fluids driven by, among other things, the fracking revolution has introduced a much higher degree of uncertainty in the market. For example, a new fluid from a previously unproduced formation having an API Gravity of 58° may yield a comparable amount of kerosene as a traditional product with an API Gravity of 42°. In addition, new drilling and production methodologies are constantly bringing previously unseen hydrocarbon slates to the market and the traditional methods of valuation of these slates are no longer as reliable as they once were.

In addition to the increased diversity in production sources, the supply dynamics have greatly changed with the increase in domestic supply. A much larger portion of a refinery's throughput is delivered via common pipeline infrastructure as opposed to large vessels, as was historically the case. This allows much more opportunity for blending discrete products together and adds uncertainty of the quality of a product due to the lack of visibility past a relative density proxy. For example, a supplier could blend a very light product with a very heavy product, both of which trade at a large discounts to established benchmarks, and sell it as a benchmark grade product. However, this type of blended product slate may not yield the valuable product slate the refiner believes it is purchasing.

Pricing structures are setup to float with a market based commodity benchmark, such as West Texas Intermediate ("WTI") or Brent. These benchmarks have certain quality standard qualifiers such as Total Acid Number ("TAN"), API Gravity range, maximum allowable water, and solids content. Any excess in contaminates or deviation from the allowable API Gravity results in pricing deductions. For example, an API Gravity number that is 2 degrees higher than the allowable benchmark could result in a $0.75 per barrel penalty to the producer. Condensates tend to be much lighter fluids and can have significant deviations from the posted benchmark values.

There is a need, therefore, for a spectroscopic analysis in the field that can provide visibility into the fractional distillation characteristics of a crude slate in real time. The distillation characteristics would allow the refinery to determine the products that may be made from the slate.

Traders and planners could utilize the information from the field to make much better purchasing and valuation decisions. For example, the refinery plan may call for a certain number of gallons of jet fuel to be produced. The purchasing agents could look at the available supply's distillation yield characteristics and buy the most efficient material, or combination of materials to ensure optimal yields. In fact, they would pay a premium to ensure they met the quotas set out in the plan to maximize profitability.

SUMMARY OF THE INVENTION

Various embodiments of the present invention are directed towards a system of spectroscopic devices deployed amongst the fluid infrastructure of hydrocarbon fluids with the purpose of providing more visibility into the characteristics of those fluids. The hydrocarbon fluids may be analyzed at any point along the infrastructure, including at the source of production or at the point where two or more fluids are blended together and the output characterized in an attempt to optimize refinery operations. The distillation characteristics, determined via spectroscopy, can provide a much more accurate assessment of the true value of a product than is currently available.

The spectroscopic information enables processors to determine the quality and quantity of refined products they can produce from a fluid and, therefore, provides information with which they can make a better assessment of true value of the fluid. The overall information system built on the data from a distributed network of spectroscopic devices provides a valuation platform that can be used to make more informed purchasing decisions. It may also be used to create blends that optimize the efficiency of refining operations.

The foregoing has outlined rather broadly certain aspects of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

The present invention is directed to improved methods and systems for, among other things, enabling parties to ascertain the characteristics of hydrocarbon fluid, in real time, to better assess the quality, quantity and value of refined products they can produce from the fluid. The configuration and use of the presently preferred embodiments are discussed in detail below. It should be appreciated, however, that the present invention provides many applicable inventive concepts that can be embodied in a wide variety of contexts other than as described herein. Accordingly, the specific embodiments discussed are merely illustrative of specific ways to make and use the invention, and do not limit the scope of the invention. In addition, the following terms shall have the associated meaning when used herein:

"crude slate" means the list of all crude oils processed by a refinery, with each particular crude oil having its own set of characteristics and contaminants;

"fluid infrastructure" means any production, transportation, storage or other infrastructure used in connection with the collection, processing, storage, transmission or distribution of a fluid including, without limitation, if the fluid is a hydrocarbon, any infrastructure between the wellhead and the point of retail delivery;

"fluid" means any liquid, including but not limited to crude oil;

"NIR" and "near infrared" mean the wavelength range between approximately 1300 to 2500 nanometers, or 1.3 to 2.5 micrometers; and "product slate" means the relative quantities of petroleum products produced by a refinery which is dependent, in part, on the properties of the crude oil being refined.

As described above, various embodiments of the present invention are directed towards a system of spectroscopic devices deployed amongst the fluid infrastructure of hydrocarbon fluids with the purpose of providing more visibility into the characteristics of those fluids at an early stage. The information includes, for example, the factional distillation characteristics, physical properties, and the types and amounts of contaminates in a stream of the fluid. The fractional distillation characteristics can be expressed as liquid volume yields distilled out over a given temperature range (e.g., the 200° F.-310° F. range of a sample may yield 17% of the overall liquid volume of the sample) or a percentage boiled off by a specific temperature (e.g., 50% of the crude boils off by the time the temperature reaches 500° F.).

Figure 1:
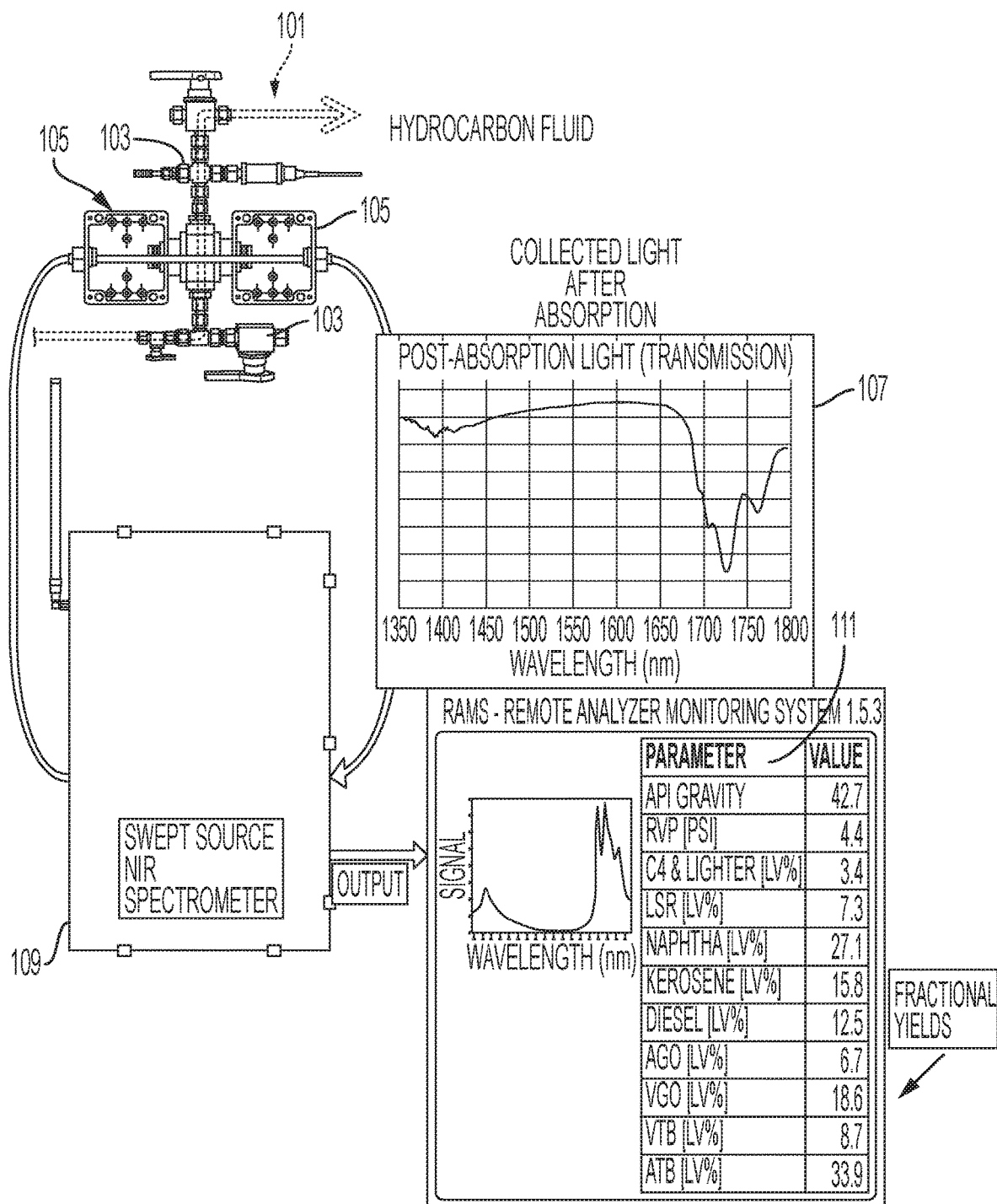
FIG. 1 is a graphic representation of one embodiment of the present invention in which a hydrocarbon is tested and information regarding post-absorption light is transmitted to a spectrometer.

Referring now to FIG. 1 in which the chemical composition of a hydrocarbon fluid 101 within a fluid infrastructure 103 may be measured using spectroscopic devices 105 that transfer an absorption spectrograph 107 to a spectrometer 109. The spectroscopic devices 105 may be placed at various locations within the fluid infrastructure 103 and the spectrometer 109 be located locally or remotely. In some embodiments, the frequency and amplitude are constantly monitored and fed back to the spectrometer 109 to maintain consistency from scan to scan. The spectrometer 109 converts the spectrograph 107 into a set of parameters 111 that corresponds to the wavelengths present in the spectrograph 107.

One spectroscopic device that may be used to determine the chemical composition of a hydrocarbon fluid is a swept source laser with a tuning range in the near infrared spectrum. Swept source laser spectroscopy is especially adept at this type of testing when the laser is tuned over a scan range in the near infrared ("NIR") and the beam contains the photonic density necessary to transmit though opaque materials. The NIR scan range may, for example, include a range of 1300 nm-2500 nm.

Figure 2:
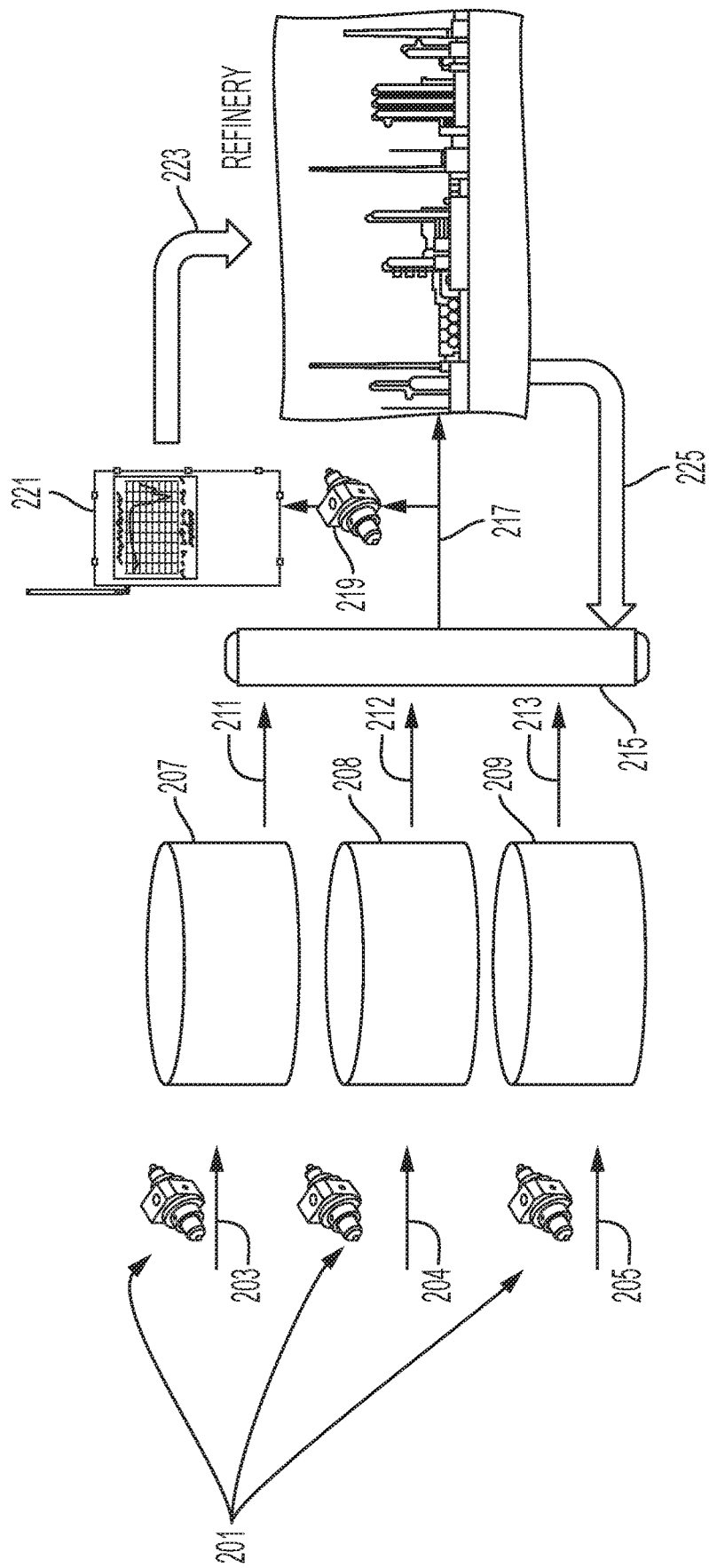
FIG. 2 is a graphic representation of one embodiment of the present invention in which spectroscopic devices provide information regarding a hydrocarbon fluid to a refinery to adjust blending.

The swept source platform is one important breakthrough, in that it enables the photonic density necessary to provide good signal to noise ratios and penetrate opaque fluids, such as those found in a fluid infrastructure of hydrocarbon fluids. Another important factor in the spectroscopic platform is its ability to be remotely deployed in almost any ambient condition and maintain a stable signal via thermal management of the internal components. Swept source lasers or scanning lasers provide sufficient signal and resolution to enable penetration through thick fluids, including low API gravity oil, to determine parameters 111 such as API Gravity, Reid vapor pressure, C4 and lighter separation, LSR, naphtha, kerosene, diesel, AGO, VGO, VTB and ATB.

Where large volumes of crude oil are stored, the spectroscopic devices may be installed on the inlets to each storage facility and the outlets of any blending operations. Referring now to FIG. 2, wherein the inlet monitors 201 may, for example, monitor the feedstock to ensure the incoming fluid meets the classification criteria for a given storage container. The inlet monitors 201 may also be able to characterize the amount of variability in quality of the fluid that is contained in a storage facility. This information may be used to predict stratification propensities or potential incompatibilities among various fluids.

In some instances, various crudes oils are blended, for example, to create an optimal feedstock that will boil off evenly for a given tower configuration or to optimize the utilization of processing equipment. Downstream of any blending operations, the spectroscopic devices may provide verification that the new feedstock has the right boiling point distribution and that contaminates do not exceed allowable levels. In some embodiments, the information feeds from the downstream devices are communicatively coupled with the processing facility and act as a feedback loop where the blend is modified in real-time to produce a desired change in processing yield or remove a bottleneck Referring now back to FIG. 2 which shows one such arrangement in which information processed from a storage facility is transferred to a refinery. Inlet monitors, 201 determine the characteristics and amount of variability in the fluid 203, 204, 205 that is fed to storage containers 207, 208, 209 in the storage facility. Stored fluid 211, 212, 213 flows to a blend header 215 where the streams 211, 212, 213 are blended to produce an output fluid stream 217. Outlet monitor 219 provides information to spectrometer 221 and, as previously described, information 223 regarding the characteristics of the blended fluid information is provided to the refinery. Upon review, the refinery may elect to provide information 225 back to the blend header 215 requesting or requiring that the characteristics of the output fluid stream 217 be modified.

The spectroscopic devices may alternatively, or additionally, be installed at any point along the crude production and processing lifecycle. They may be wirelessly connected or hard wired to send data to a central gathering location where producers or others can view the properties of the crude oil. They may be installed at the exact point of production (e.g., a wellhead) or, as described above, at gathering locations where multiple sources of production are comingled, stored, and/or blended to create all new compositions. The spectroscopic devices may also be installed on trucks where the composition, physical properties, and distillation information is wirelessly transmitted to dispatch office that determines the delivery point for the load of crude oil.

Figure 3:
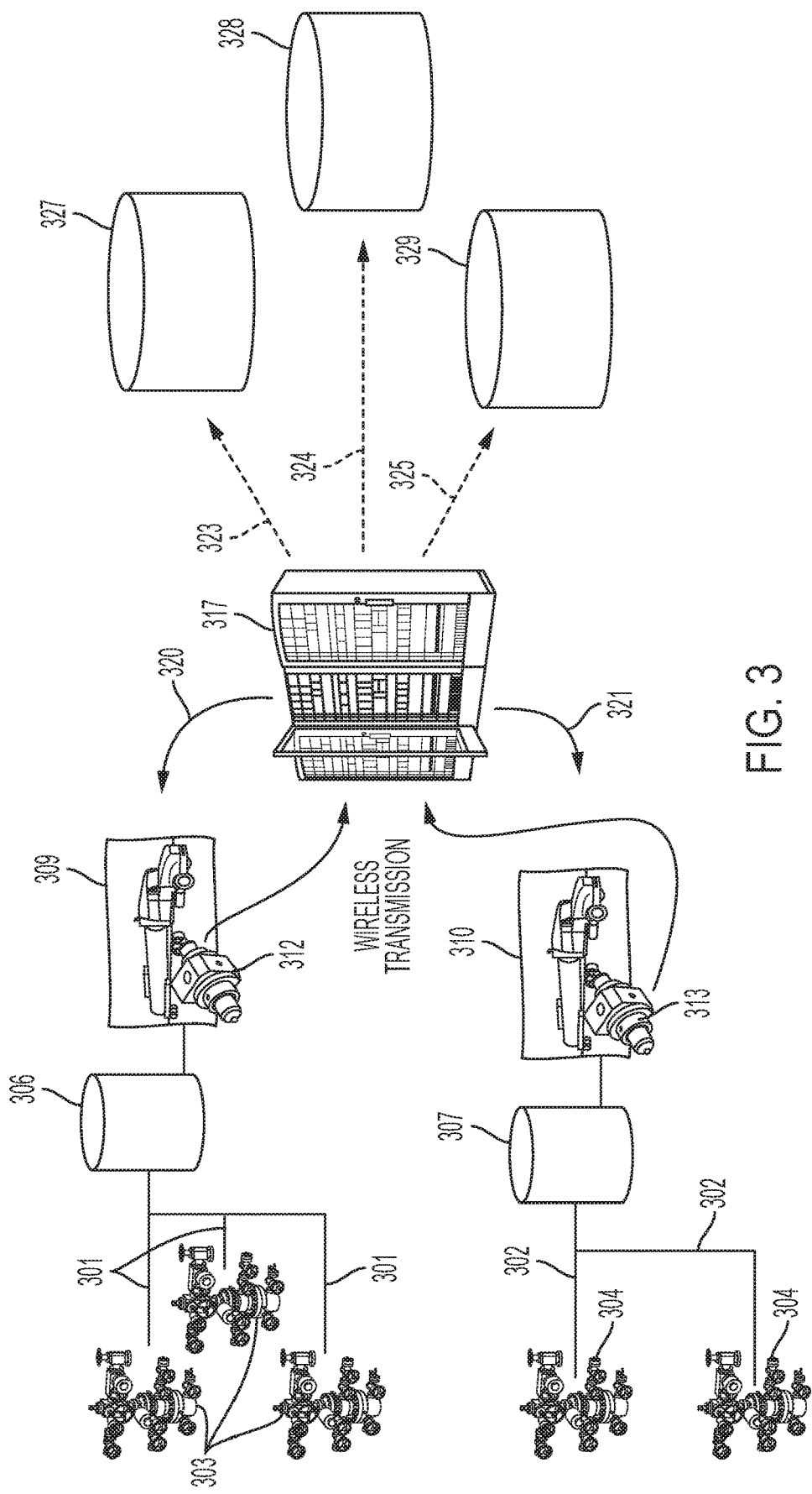
FIG. 3 is a graphic representation of one embodiment of the present invention in which spectroscopic devices provide information regarding a hydrocarbon fluid to tank trucks for logistical purposes.

In one example of the foregoing embodiment which is graphically depicted in FIG. 3, crude oil 301, 302 flows from well heads 303, 304 to lease tanks 306, 307 and, subsequently, to tank trucks 309, 310. Spectroscopic devices 312, 313 transmit information regarding the characteristics of the fluid in each truck 309, 310 to a data/dispatch center 317. Based on the blend of fluid desired in each storage tank 327, 328, 329, the data/dispatch center provides information 320, 321 to the drivers of the trucks 309, 310 to transport their respective fluids to one or more of the respective tanks 327, 328, 329, thereby efficiently optimizing the composition of the fluid in each tank 327, 328, 329.

In some embodiments, distributed installed spectroscopic devices that are installed in proximity to the production sources could feed information to a central location where crude purchasing agents receive visibility into quality information that is not available from existing instrumentation. Those agents could then make purchasing and pricing decisions that would not be possible based on currently available information. For example, a crude oil purchaser may be willing to pay more for a supply than traditional metrics would warrant because they have increased confidence that the efficiency gains at the refinery would more than outweigh the premium.

Refiners often generate purchasing plans based on the configuration of their facilities and the current prices of the crude products they can produce. Having more information on the refined yields of the feedstocks currently available before it is purchased and distilled provides tremendous forecasting value to the refiner. As the market changes and influences the purchasing plan, purchasing agents may react more quickly and procure the best feedstocks to maximize profitability.

Figure 4:
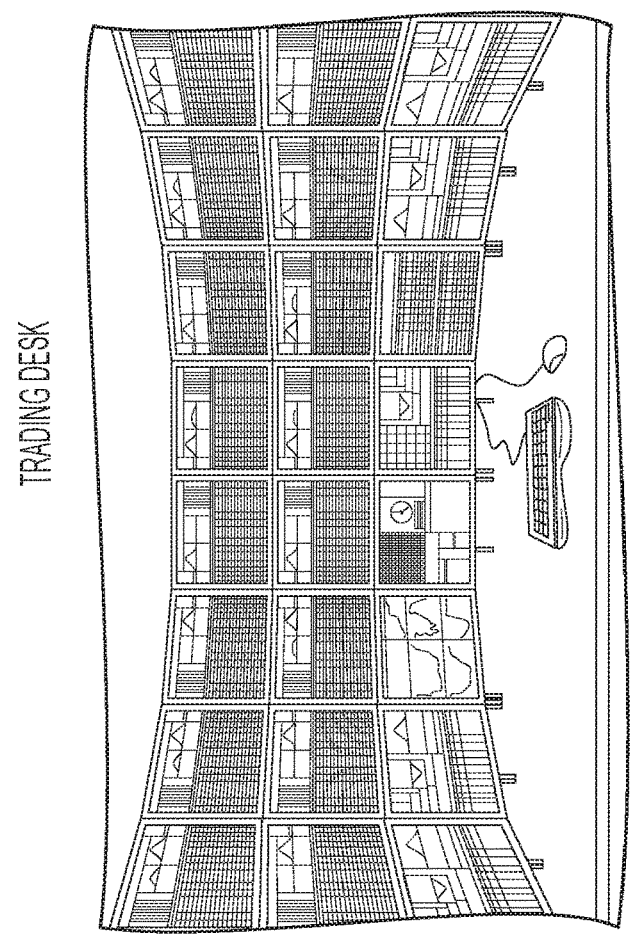
FIG. 4 is a graphic representation of one embodiment of the present invention in which spectroscopic devices provide information regarding a hydrocarbon fluid directly from the well heads to a trading desk.
Figure 4:
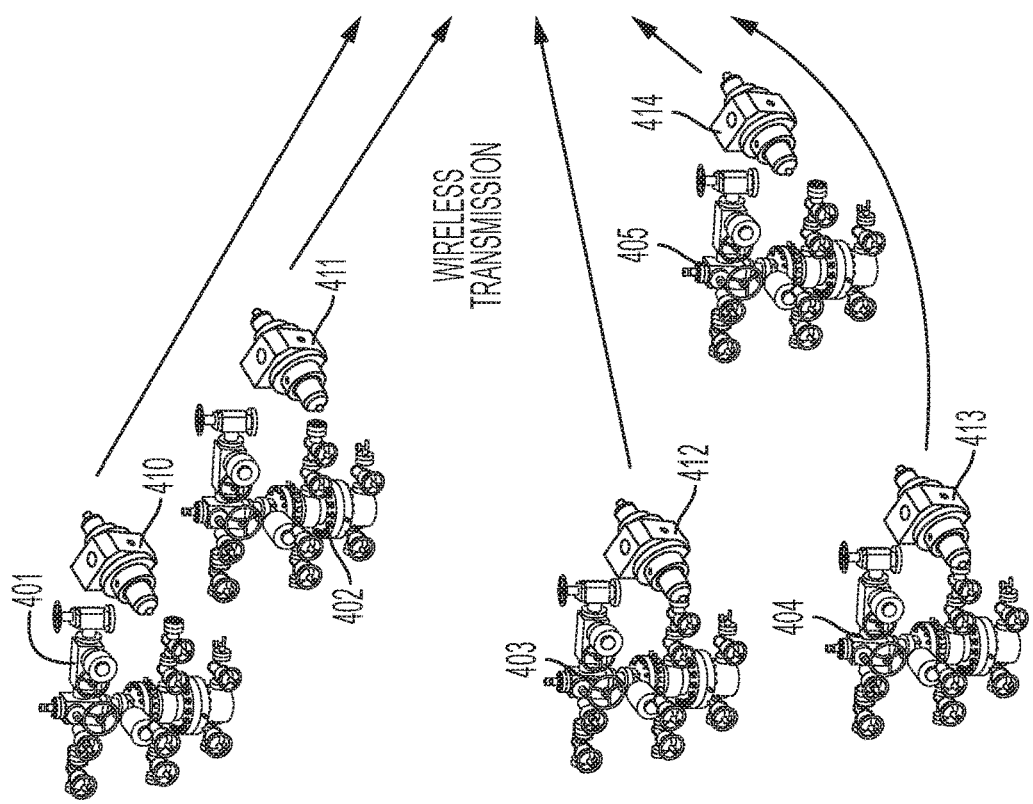

In one example of the foregoing, depicted in FIG. 4, information regarding the make-up of the crude oil is provided directly from spectroscopic devices 410, 411, 412, 413, 414 located at the wellheads 401, 402, 403, 404, 405 to the trading desk, thereby providing market managers with immediate, direct information regarding the characteristics of the oil being pumped.

The overall information system created from the data generated by a fleet of deployed swept source spectrometers would also be of value to the producers of the crude. They could use the information to better market their product and get the best price possible. The information is also useful for reservoir management and influence future drilling plans.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for fluid valuation known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

We claim:

1. A system for modifying a blended crude oil stream, comprising:
    two or more spectroscopic devices positioned at two or more wellheads, the spectroscopic devices acquiring information regarding the characteristics of crude oil transmitted from the two of more wellheads to two or more storage tanks;
    a blend header receiving crude oil from the two or more storage tanks, the blend header blending the crude oil from the two or more storage tanks to create an output stream;
    a spectroscopic device at the blend header monitoring the output stream and providing information regarding the characteristics of the output stream to a refinery in real time; and
    the refinery providing information back to the blend header regarding adjustments required to the blending of the crude oil from the two or more storage tanks to modify the output stream.

2. The system for modifying a blended crude oil stream of claim 1, wherein the two or more spectroscopic devices are swept source lasers.

3. The system for modifying a blended crude oil stream of claim 1, wherein the two or more spectroscopic devices are swept source lasers having a wavelength range of between approximately 1300 and 2500 nanometers.

4. The system for modifying a blended crude oil stream of claim 1, wherein the refinery provides information back to the two or more spectroscopic devices positioned at the two or more wellheads to make adjustments to the flow of crude oil from the two or more wellheads to the two or more storage tanks.

5. The system for modifying a blended crude oil stream of claim 1, wherein the information regarding the characteristics of the output stream includes one or more of API Gravity, Reid vapor pressure, C4 and lighter separation, LSR, naphtha, kerosene, diesel, AGO, VGO, VTB and ATB.

6. The system for modifying a blended crude oil stream of claim 1, wherein the information regarding the characteristics of the output stream includes API Gravity, Reid vapor pressure, and C4 and lighter separation.

7. A system for valuing a product slate, comprising:
two or more spectroscopic devices positioned at two or more wellheads, the spectroscopic devices providing crude slate information regarding the crude oil transmitted from the two or more wellheads to a producer in real time;
a product slate prepared by the producer, wherein the product slate is dependent on the crude slate; and
the producer using the crude slate information received from the two or more spectroscopic devices to determine the value of the product slate.

8. The system for valuing a product slate of claim 7, wherein the two or more spectroscopic devices are swept source lasers.

9. The system for valuing a product slate of claim 7, wherein the two or more spectroscopic devices are swept source lasers having a wavelength range of between approximately 1300 and 2500 nanometers.

10. For valuing a product slate of claim 7, wherein the crude slate information includes one or more of API Gravity, Reid vapor pressure, C4 and lighter separation, LSR, naphtha, kerosene, diesel, AGO, VGO, VTB and ATB.

11. The system for valuing a product slate of claim 7, wherein the information regarding the crude slate information includes API Gravity, Reid vapor pressure, and C4 and lighter separation.

12. A system for directing the transportation of crude oil, comprising:
two or more spectroscopic devices positioned at two or more wellheads, the spectroscopic devices acquiring information regarding the characteristics of crude oil transmitted from the two or more wellheads to two or more tank trucks;
tank truck spectroscopic devices positioned at each of the two or more tank trucks providing information regarding the characteristics of crude oil in the two or more tank trucks to a dispatch center in real time; and
the dispatch center providing transportation instructions to the two or more tank trucks based on the characteristics of crude oil in the two or more tank trucks.

13. The system for directing the transportation of crude oil of claim 12, wherein the two or more spectroscopic devices are swept source lasers.

14. The system for directing the transportation of crude oil of claim 12, wherein the two or more spectroscopic devices are swept source lasers having a wavelength range of between approximately 1300 and 2500 nanometers.

15. The system for directing the transportation of crude oil of claim 12, wherein the information regarding the characteristics of the crude oil includes one or more of API Gravity, Reid vapor pressure, C4 and lighter separation, LSR, naphtha, kerosene, diesel, AGO, VGO, VTB and ATB.

* * * * *